United States Patent [19]

Larkin et al.

[11] Patent Number: 4,825,000
[45] Date of Patent: Apr. 25, 1989

[54] PHENYL GLYCIDYL ETHER MODIFIED POLYOXYALKYLENE DIAMINES AND EPOXY RESIN COMPOSITIONS THEREFROM

[75] Inventors: John M. Larkin; Robert L. Zimmerman; Michael Cuscurida; Harold G. Waddill, all of Austin, Tex.

[73] Assignee: Texaco Inc., White Plains, N.Y.

[21] Appl. No.: 891,086

[22] Filed: Jul. 31, 1986

[51] Int. Cl.$^4$ .............................................. C07C 93/06
[52] U.S. Cl. ........................................ 564/347; 564/346; 528/87
[58] Field of Search ................................ 564/346, 347

[56] References Cited

U.S. PATENT DOCUMENTS

| | | | |
|---|---|---|---|
| 2,681,901 | 6/1954 | Wiles et al. | 260/47 |
| 2,839,480 | 6/1958 | Ott et al. | 260/18 |
| 3,222,300 | 12/1965 | Loew | 260/2.5 |
| 3,236,895 | 2/1966 | Lee et al. | 260/584 |
| 3,654,370 | 4/1972 | Yeakey | 260/584 B |
| 3,875,072 | 4/1975 | Waddill | 252/182 |
| 4,766,245 | 8/1988 | Larkin et al. | 564/474 |

*Primary Examiner*—Robert V. Hines
*Attorney, Agent, or Firm*—Jack H. Park; Kenneth R. Priem; Richard A. Morgan

[57] ABSTRACT

A series of polyoxyalkylene diamines modified with phenoxy groups is disclosed. This series of diamines is of the general formula:

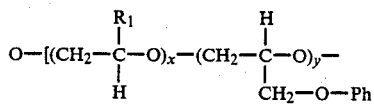

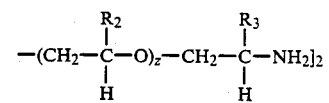

wherein $R_1$ and $R_2$ are independently hydrogen or an alkyl of 1 to 4 carbon atoms, $R_3$ is a alkyl of 1 to 4 carbon atoms, Ph is phenyl, x ranges from 2 to 40, y ranges from 1 to 20 and z ranges from 1 to 40.

These diamines are cured with liquid epoxy resins. The cured resins demonstrated improved tensile strength and modulus, elongation and flexural strength and modulus over a commercially used curative.

The diamines are also useful in RIM elastomers, in polyamides and as chain extenders in polyurethane foams.

6 Claims, No Drawings

PHENYL GLYCIDYL ETHER MODIFIED POLYOXYALKYLENE DIAMINES AND EPOXY RESIN COMPOSITIONS THEREFROM

BACKGROUND OF THE INVENTION

1. Field of the Invention

The invention relates to a series of polyoxyalkylene diamines modified with phenyl groups through ether linkages. The invention also relates to epoxy resin compositions cured with these diamines.

2. Description of the Useful Arts

Epoxy resins constitute a broad class of polymeric materials having a wide range of physical characteristics. The resins are characterized by epoxide groups which are cured by reaction with certain catalysts or curing agents to provide cured epoxy resin compositions with certain desirable properties. One such class of curing agents is, generally, the amines. The most commonly used amine curing agents are aliphatic amines such as diethylenetriamine, triethylenetetramine and the like and/or polyoxyalkylene polyamines; such as polyoxypropylenediamines and triamines and their amino propyl derivatives.

Epoxy resin compositions having improved physical properties are obtained by employing polyoxyalkyleneamines, and polyoxyalkylenediamines in particular, as curing agents.

U.S. Pat. No. 3,222,300 describes polyoxyalkylene glycols modified with glycidyl ethers containing three hydroxyl groups. Those polyhydroxyl components are reacted with polyisocyanate to yield cellular polyurethanes.

U.S. Pat. No. 3,326,895 describes a series of polyoxyalkylene diamines. The diamines are used for curing epoxy resins.

U.S. Pat. No. 3,654,370 describes a process for preparing polyoxyalkylene diamines. These diamines are prepared by the addition of alkylene oxide to an aliphatic polyhydric alcohol. The resulting polyoxyalkylene polyols are reacted with ammonia and hydrogen over a catalyst prepared by the reduction of a mixture of the oxides of nickel, copper and chromium. The diamines are used as curing agents for epoxy resins.

SUMMARY OF THE INVENTION

The invention is a series of diamines having the formula:

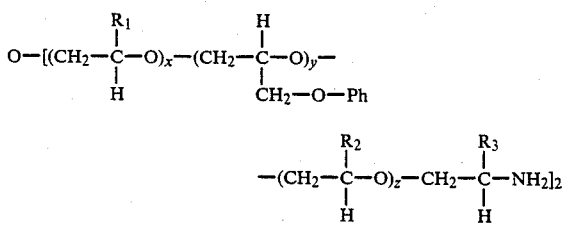

$R_1$ and $R_2$ are independently hydrogen or an alkyl of 1 to 4 carbon atoms and $R_3$ is an alkyl of 1 to 4 carbon atoms. Ph is a phenyl radical. In the subscripts, x ranges from 2 to 40, y ranges from 1 to 20 and z ranges from 1 to 40.

These diamines have a number of uses. Epoxy resins cured with these diamines demonstrate improved tensile strength and modulus; elongation and flexural strength and modulus. The diamines are also useful in RIM elastomers, in polyamines and as chain extenders in polyurethane foams.

DESCRIPTION OF THE PREFERRED EMBODIMENTS

Polyoxyalkylene polyamines of the present invention are prepared by a series of reactions, each one of which is well known in the art. First, the precursor polyalkylene ether glycol is prepared by acid or base catalyzed condensation of an oxyalkylation-susceptible glycol with any alkylene oxide having 2 to 6 carbon atoms, such as ethylene oxide, propylene oxide and butylene oxide. After digestion, phenyl glycidyl ether is condensed with the growing polymer chain. The polymer chain is completed with the final addition of alkylene oxide.

The polyoxyalkylene glycol is then aminated to yield the corresponding diamine. Raney nickel is a suitable amination catalyst. It was found that Raney nickel converted some of the phenoxy groups to methyl groups. However, it is reported that molybdenum promoted Raney nickel does not cause phenoxy group hydrogenolysis. Therefore, molybdenum or aluminum promoted Raney nickel, described, for example, in U.S. patent applications Ser. No. 707,126 filed Mar. 1, 1985 now U.S. Pat. No. 4,766,245: issued Aug. 23, 1988 and Ser. No. 739,595 filed May 31, 1985 now abandoned both incorporatd herein by reference are more suitable. U.S. Pat. No. 3,654,370 to Yeakey incorporated herein by reference describes another amination catalyst. In this patent, a polyoxyalkylene polyol is aminated with ammonia and hydrogen at a temperature of 150° to 275° C. and a pressure of 500 to 5000 psig over a catalyst prepared by the reduction of a mixture of the oxides of nickel, copper and chromium.

These diamines when cured with liquid epoxy resins show improved properties over a polyoxyalkylene diamine used commercially to cure epoxy resins. Diamines in the inventive series are particularly suited to use as epoxy resin curatives when they have a molecular weight of 400 to 10,000, preferably 1000 to 7,000. To achieve this molecular weight range the proportionate amount of monomer are such that x ranges from 2 to 10, y ranges from 1 to 10 and z ranges from 1 to 10.

These preferred diamines when cured with epoxy resins have demonstrated improved tensile strength and modulus. The reason for these improved properties is not known with absolute certainty. It is theorized that the electrostatic repulsion between phenyl groups and alkyl groups accounts for stiffening along the polymer chain. This is quantified by specifying that the ratio of $y/(x+z)$ ranges from 0.05 to 0.5. The stiffening without chemical bonding yields a stiff epoxy resin composition which does not crack when flexed. The examples demonstrate the improvement of the inventive diamines over smilar diamines which do not contain phenyl groups positioned between alkyl groups along the polymer chain.

The liquid epoxy resins which are cured with the diamines of the present invention are polyepoxide containing compounds having an average of at least 1.8 reactive 1,2-epoxy molecule. These polyepoxide materials can be monomeric or polymeric, saturated or unsaturated, aliphatic, cycloaliphatic, aromatic or heterocyclic, and may be substituted if desired with other substituents besides the epoxy groups, e.g., hydroxyl groups, ether radicals, aromatic halogen atoms and the like.

Preferred polyepoxides are those of glycidyl ethers prepared by epoxidizing the corresponding alkyl ethers or reacting, by known procedures, a molar excess of epichlorohydrin and an aromatic polyhydroxy compound, i.e., isopropylidene bisphenol, novolac, resorcinol, derivatives of aromatic amines, etc. The epoxy derivatives of methylene or isopropylidene bisphenols are especially preferred. The condensation product of epichlorohydrin with bisphenol A is particularly preferred.

A widely used class of polyepoxides which are useful according to the present invention includes the resinous epoxy polyethers obtained by reacting an epichlorohydrin, such as epichlorohydrin, and the like, with either a polyhydric phenol or a polyhydric alcohol. Typically the epoxy resins have an average of at least 1.8 reactive, 1,2-epoxy groups per molecule. An illustrative, but by no means exhaustive, listing of suitable dihydric phenols includes 4,4'-isopropylidene bisphenol, 2,4'-dihydroxydiphenylethylmethane, 3,3'-dihydroxydiphenyldiethylmethane, 3,4'-dihydroxydiphenylmethylpropylmethane, 2,3'-dihydroxydiphenylethylphenylmethane, 4,4'-dihydroxydiphenylpropylphenylmethane, 4,4-dihydroxydiphenylbutylphenylmethane, 2,2'-dihydroxydiphenylditolylmethane, 4,4'-dihydroxydiphenyltolylmethane and the like. Other polyhydric phenols which may also be coreacted with an epihalohydrin to provide these epoxy polyethers are such compounds as resorcinol, hydroquinone, substituted hydroquinones, e.g., methylhydroquinone, and the like.

Among the polyhydric alcohols which can be coreacted with an epihalohydrin to provide these resinous epoxy polyethers are such compounds as ethylene glycol, propylene glycols, butylene glycols, pentane diols, bis-(4-hydroxycyclohexyl)dimethylmethane, 1,4-dimethylolbenzene, glycerol, 1,2,6-hexanetriol, trimethylolpropane, mannitol, sorbitol, erythritol, pentaerythritol, their dimers, trimers and higher polymers, e.g., polyethylene glycols, polypropylene glycols, triglycerol, dipentaerythritol and the like, polyallyl alcohol, polyhydric thioethers, such as 2,2'-,3,3'-tetrahydroxydipropropylsulfide and the like, mercapto alcohols such as monothioglycerol, dithiogylcerol and the like, polyhydric alcohol partial esters, such as monostearin, pentaerythritol monoacetate and the like, and halogenated polyhydric alcohols such as the monochlorohydrins of glycerol, sorbitol, pentaerythritol and the like.

Another class of polymeric polyepoxides which can be amine cured and are in accordance with the present invention includes the epoxy novolac resins obtained by reacting, preferably in the presence of a basic catalyst, e.g., sodium or potassium hydroxide, an epihalohydrin, such as epichlorohydrin, with the resinous condensate of an aldehyde, e.g., formaldehyde, and either a monohydric phenol, e.g., phenol itself, or a polyhydric phenol. Further details concerning the nature and preparation of these epoxy novolac resins can be obtained in Lee, H. and Neville, K., *Handbook of Epoxy Resins,* McGraw Hill Book Co., New York, 1967.

It will be appreciated by those skilled in the art that the polyepoxide compositions which are useful according to the practice of the present invention are not limited to those containing the above described polyepoxides, but that these polyepoxides are to be considered merely as being representative of the class of polyepoxides as a whole.

In the process of the present invention, the curative agent and optionally an accelerator are mixed to form a compatible solution. The epoxy base resin is added and the components thoroughly contacted by mixing until a homogeneous mixture is obtained.

The curative agent is usually added to the formulation in such an amount that there is one reactive hydrogen atom in the curing component for each epoxy group in the epoxy resin component. These are known as stoichiometric quantities. The stoichometric quantity can be calculated from the knowledge of the chemical structure and analytical data on the component. Stoichiometry unfortunately is not always calculable. For systems of the present invention, the proper amount of curative is the amount necessary to provide the best desired properties. This amount must be determined experimentally and can be accomplished by routine procedures known in the art. Generally the number of equivalents of reactive curative groups is from about 0.8 to 1.2 times the number of epoxide equivalents present in the curable epoxy resin composition, with from 0.9 to a stoichiometric amount being preferred. The exact amount of constituents will depend, as mentioned, primarily on the application for which the cured resin is intended.

For many applications, curing may be accomplished at ambient conditions. For development of optimum achievable properties, however, curing at elevated temperature is necessary. The curing temperature range acceptable in this invention is from about 120° C. to about 180° C. for about 1 to 3 hours. Preferably curing is done at about 125° C. for 1 to 2 hours.

Optionally, the epoxy resin formulations of the present invention can include an accelerator to speed the amine cure of the epoxy resin. In several applications, an accelerator is beneficial, especially when an epoxy resin is used as an adhesive in a flammable environment, thus making prolonged elevated temperature cure inconvenient or even hazardous. Lee, H. and Neville, K., *Handbook of Epoxy Resins,* pp. 7–14, describes the use of certain amine-containing compounds as epoxy curative agent-accelerators.

Many accelerators are known in the art which can be utilized in accordance with the instant invention. Examples include salts of phenols, salicylic acids; amine salts of fatty acids such as those disclosed in U.S. Pat. No. 2,681,901; and, tertiary amines such as those disclosed in U.S. Pat. No. 2,839,480. A preferred accelerator in accordance with the instant invention is disclosed in U.S. Pat. No. 3,875,072, G. Waddill. That accelerator comprises a combination of piperazine and an alkanol amine in a weight ratio of about 1:8 to 1:1. The above amount of accelerator is admixed with the polyoxyalkylene diamine curative agent in amount of from about 10 to 50 parts by weight accelerator to 100 parts by weight of the curing agent.

The following Examples are illustrative of the nature of the present invention but are not intended to be limitative thereof.

EXAMPLE I

Preparation of phenyl glycidyl ether-modified polyoxyalkylene glycols

Into a one-half gallon kettle was charged 227 g of 400 molecular weight polypropylene glycol initiator (alkalinity, mg KOH/g 27.8) The reactor was then purged with prepurified nitrogen. The reactor was heated to 100° C. with nitrogen purging. Propylene oxide (331 g) was added and reacted at 110°–115° C. at 50 psig over a two-hour period. The reaction mixture was then digested for 30 minutes. Phenyl glycidyl ether (345 g) was then charged into the kettle as rapidly as possible. After a one-half hour digestion an additional 331 g propylene oxide was reacted at 110°–115° C. over a 1.5 hour period. After digestion to an equilibrium pressure, the alkaline product was neutralized with 38 g magnesium silicate (Magnesol ® 30/40) which was added as an aqueous slurry. This was followed by the addition of 1.1 g di-tert-butyl p-cresol. The neutralized product was then vacuum stripped to a minimum pressure, nitrogen stripped, and filtered. Properties of the finished product were as follows:

| Properties | Run No. | | | |
|---|---|---|---|---|
| | 6056-36 | 6056-40 | 6056-44 | 6056-49 |
| Acid no., mg KOH/g | — | 0.003 | — | 0.002 |
| Hydroxyl no., mg KOH/g | 59.5 | 57.3 | 58.9 | 59.2 |
| Water, wt. % | — | 0.07 | — | 0.06 |
| Unsaturation, meq/g | 0.039 | — | 0.036 | 0.035 |
| pH in 10:6 isopropanol-water | — | 7.5 | 7.6 | 7.5 |
| Color, Pt—Co | — | — | 150 | 250 |
| Sodium, ppm | 0.5 | 0.2 | 0.5 | 0.4 |
| Potassium, ppm | 5.0 | 1.2 | 2.24 | 2.4 |
| Viscosity,°F., cs | | | | |
| 77 | 833 | 889 | — | 822 |
| 100 | 350 | 364 | — | 339 |

EXAMPLE II

Preparation of a diamine from ether-modified polyoxyalkylene glycol of example I The four runs of example I were combined, filtered fed continuously to a tubular reactor containing 92 ml of 6×8 mesh Raney nickel maintained at 210° C. and 2000 psig. The feed rate was 62.5 g/hr. Ammonia at 56.7 g/hr and hydrogen at 5 l/hr were also fed to the reactor concurrently. Reactor effluent was stripped on a rotary evaporator at 99° C./25 mm Hg. Analysis of the product indicated 1.24 meq/g total acetylatables, 1.13 meq/g total amines, 1.09 meq/g primary amine, and 0.01 wt.% water. The NMR spectra of the product was consistent with the following structure:

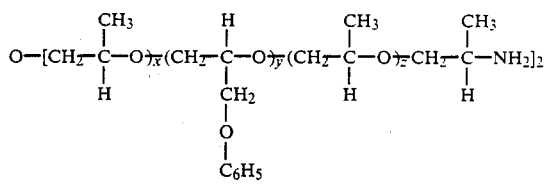

wherein x=8.5; y=1.5 and z=5

The relative number of phenyl/methyl groups in the polyether backbone is 0.89/10.

EXAMPLE III

Curing of Liquid Epoxy Resins

Formulations and properties of the cured epoxy resins are shown in the following table.

| | Sample No. | | | | | | | | |
|---|---|---|---|---|---|---|---|---|---|
| | 6087-46A | 6087-46B | 6087-46C | 6087-46D | 6087-46E | 6031-72A | 6031-72B | 6031-72C | 6031-72D |
| Formulation | | | | | | | | | |
| Liquid epoxy resin (EW 185) | 100 | 100 | 100 | 100 | 100 | 100 | 100 | 100 | 100 |
| Jeffamine ® D-400 | 57 | 55.5 | 54.0 | 52.0 | 49.8 | 55.4 | 53.7 | 51.7 | 49.2 |
| Jeffamine ® D-2000 | — | 6.5 | 13.0 | 22.0 | 33.2 | — | — | — | — |
| Diamine of Example 2 | — | — | — | — | — | 6.1 | 13.4 | 22.1 | 32.9 |
| Properties of cured ⅛ in. castings[1] | | | | | | | | | |
| Izod impact strength, ft-lbs/in | 0.14 | 0.14 | 0.10 | 0.17 | 5.6 | 0.12 | 0.11 | 0.13 | 3.1 |
| Rheometrics ® Impacter, total energy, in-lb | 52 | 59 | 87 | 81 | 79 | 45 | 76 | 95 | 122 |
| Tensile strength, psi | 7700 | 6700 | 4400 | 2600 | 1400 | 6900 | 4600 | 2800 | 1700 |
| Tensile modulus, psi | 411000 | 367000 | 293000 | 107000 | 12100 | 346000 | 283000 | 135000 | 20700 |
| Elongation at break, % | 5.0 | 4.7 | 41 | 85 | 73 | 10.0 | 57.4 | 83 | 83 |
| Flexural strength, psi | 12300 | 11600 | 8600 | 3000 | 400 | 11700 | 8600 | 3500 | 700 |
| Flexural modulus, psi | 411000 | 389000 | 269000 | 108000 | 10900 | 385000 | 278000 | 130500 | 34000 |
| HDT, °C., 264 psi/66 psi | 44/47 | 43/43.5 | 37/40 | 30/35 | <25/<25 | 40/42 | 38/40 | 26/33 | 25/28 |
| Shore D hardness, 0–10 sec. | 71–67 | 69–65 | 65–61 | 61–52 | 48–35 | 62–59 | 62–57 | 58–50 | 50–38 |
| Compression strength at failure, psi | 33500 | 30700 | 47900 | 39900 | 50200 | 43100 | 46500 | 48200 | 43800 |
| % Weight gain, 24 hour water boil | 2.8 | 2.8 | 2.8 | 2.8 | 2.8 | 3.0 | 3.1 | 3.1 | 3.0 |
| % Weight gain, 3 hour acetone boil | 21.7 | 24.5 | 23.7 | 31.9 | 40.4 | 23.8 | 24.8 | 31.7 | 35.4 |

[1]Cured 2 hours 80° C., 3 hours 125° C.
Jeffamine ® D-400 structure: H$_2$HCH(CH$_3$)CH$_2$[OCH$_2$CH(CH$_3$)]$_{5.6}$NH$_2$
Jeffamine ® D-2000 structure: H$_2$NCH(CH$_3$)CH$_2$[OCH$_2$CH(CH$_3$)]$_{33.1}$NH$_2$
Both of those diamines may be synthesized according to the process of U.S. Pat. No. 3,654,370 to Yeakey.
Jeffamine ® D-400 and D-2000 are used commercially to cure epoxy resins.

| TABLE OF TEST METHODS | |
|---|---|
| Izod Impact Strength | ASTM D-256 |
| Tensile Strength | ASTM D-638 |
| Tensile Modulus | ASTM D-638 |
| Elongation Break | ASTM D-638 |
| Flexural Strength | ASTM D-790 |
| Flexural Modulus | ASTM D-790 |
| HDT | ASTM D-648 |
| Shore D Hardness | ASTM D-2240 |
| Compression strength at failure | ASTM D-695 |

The principle of the invention and the best mode contemplated for applying the principle have been described. It is to be understood that the foregoing is illustrative only and that after means and techniques can be employed without departing from the true scope of the invention defined in the following claims.

What is claimed is:

1. A diamine having the formula:

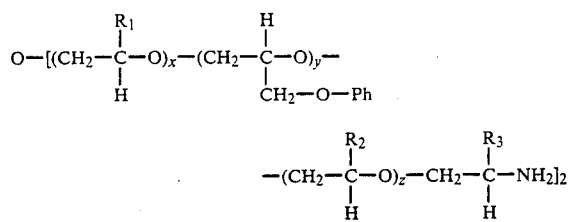

wherein $R_1$ is hydrogen or an alkyl of 1 to 4 carbon atoms, $R_2$ is hydrogen or an alkyl of 1 to 4 carbon atoms, $R_3$ is an alkyl of 1 to 4 carbon atoms, Ph is phenyl, x ranges from 2 to 40, y ranges from 1 to 20 and z ranges from 1 to 40.

2. The diamine of claim 1 wherein $R_1$, $R_2$ and $R_3$ are methyl.

3. The diamine of claim 1 wherein $R_1$, $R_2$ and $R_3$ are methyl and the ratio $y/(x+z)$ ranges from 0.05 to 0.5.

4. The diamine of claim 1 wherein $R_1$, $R_2$ and $R_3$ are methyl, x ranges from 2 to 10, y ranges from 1 to 10 and z ranges from 1 to 10.

5. The diamine of claim 1 wherein the molecular weight ranges from 400 to 10,000.

6. The diamine of claim 1 wherein the molecular weight ranges form 1000 to 7000.

* * * * *